United States Patent [19]

Kimura et al.

[11] Patent Number: 5,433,203
[45] Date of Patent: Jul. 18, 1995

[54] BONE ASSESSMENT APPARATUS AND METHOD

[75] Inventors: Shigeo Kimura; Naoki Ohtomo, both of Tokyo, Japan

[73] Assignee: Aloka Co., Ltd., Tokyo, Japan

[21] Appl. No.: 278,092

[22] Filed: Jul. 21, 1994

[30] Foreign Application Priority Data

Jul. 22, 1993 [JP] Japan .................................. 5-180541

[51] Int. Cl.$^6$ ........................ A61B 8/00; G01N 29/04
[52] U.S. Cl. ................................ 128/660.060; 73/599
[58] Field of Search ................... 128/660.010, 660.060, 128/66.030; 73/599

[56] References Cited

U.S. PATENT DOCUMENTS

| | | | |
|---|---|---|---|
| 3,847,141 | 12/1974 | Hoop . | |
| 4,202,215 | 5/1980 | Meyer | 128/660.060 X |
| 4,594,895 | 6/1986 | Fujii | 73/599 |
| 4,774,959 | 10/1988 | Palmer et al. . | |
| 4,930,511 | 6/1990 | Rossman et al. . | |
| 5,042,489 | 8/1991 | Wiener et al. . | |
| 5,054,490 | 10/1991 | Rossman et al. . | |
| 5,099,849 | 3/1992 | Rossman et al. | 128/660.060 |
| 5,218,963 | 6/1993 | Mazess | 128/661.030 |
| 5,361,767 | 11/1984 | Yakov | 128/660.060 |

OTHER PUBLICATIONS

Ophir, J. et al. "Attenuation Estimation in Reflection Progress & Prospects"; UTS Imaging V6 pp.349-395 (1984).

Andre et al., "Measurement of the velocity of ultrasound in the Human Femur in vivo," 2389 Med. Phy. pp. 324-330, vol. 7 (1980) Jul./Aug., No. 4, N.Y.

Primary Examiner—Francis Jaworski
Attorney, Agent, or Firm—Fish & Richardson

[57] ABSTRACT

A bone assessment apparatus provides a precise bone assessment based on the attenuation factor of an ultrasonic wave which has passed through a bone of a patient. A transmitting transducer and a receiving transducer are positioned at either side of the bone respectively, and an ultrasonic wave is irradiated to the bone, and passes therethrough. A transmitter/receiver provides an attenuation spectrum of the ultrasonic wave and determines a reference frequency $f_p$ peculiar to the patient at which the attenuation factor is minimum. A gradient $\Delta$ of the attenuation spectrum is calculated based on the difference between the attenuation factor $\alpha_p$ at the reference frequency $f_p$ and the attenuation factor $\alpha_q$ at a frequency $f_q$ which is spaced apart by a predetermined value from the reference frequency $f_p$. A density index $\rho_I$ is also calculated which is a gradient of the attenuation spectrum per unit thickness of the bone.

11 Claims, 2 Drawing Sheets

BONE ASSESSMENT APPARATUS AND METHOD

BACKGROUND OF THE INVENTION

1. Field of the Invention

The present invention relates to a bone assessment apparatus and bone assessing method, and more particularly to an apparatus and method for assessing a bone based on attenuation factors of an ultrasonic wave which has passed through the bone.

2. Description of the Related Art

Due to the rapid increase in the number of elderly people in the population, bone disorders such as osteoporosis and osteomalacia are becoming more common, and a great need has emerged for better diagnosis and prophylaxis.

Among bones, especially spongiosa (i.e. cancellous bone) consists of trabecula which is relatively hard and bone marrow which is relatively soft. In other words, marrow fills the spaces in the trabecula extending lengthwise and crosswise to form the spongiosa.

Bone diseases cause the bone structure to be weakened. The density of trabecula of those who are in good health is relatively high, while the density of trabecula of those who are suffering from a bone disease such as osteoporosis is relatively low.

When an ultrasonic wave is irradiated to a bone, the attenuation factor of the transmitted ultrasonic wave varies depending on the frequency. The attenuation characteristic is also varied by changes in the bone structure. When irradiating an ultrasonic wave to a bone where the trabecula is coarse, the attenuation factor of the ultrasonic wave becomes smaller.

An apparatus for diagnosing bone disease by detecting and observing the attenuation characteristics of the ultrasonic wave has been proposed in, for example, U.S. Pat. No. 4,774,959. In such an apparatus, two different frequencies are fixedly set, and an attenuation factor is obtained at each of the predetermined frequencies. Then, the gradient of the attenuation factor relative to the frequency is computed based on the difference between the two attenuation factors. However, in such a conventional apparatus, differences among individuals are not considered, and therefore, reliable bone assessment results can not be obtained.

SUMMARY OF THE INVENTION

In various experiments performed by the inventors of the present invention, it has been found that a frequency at which the attenuation factor of the ultrasonic wave becomes minimum (hereinafter referred to as a reference frequency) is different among individuals, when an ultrasonic wave is irradiated to the bone to be assessed. Namely, a reference frequency is different for each individual. Accordingly, if a gradient of the attenuation factor relative to the frequency (hereinafter referred to as a gradient of attenuation spectrum) is obtained without considering the differences in the reference frequency among individuals as is in a conventional apparatus, accurate data can not be obtained which correctly represents a condition of the bone structure.

Therefore, it is an object of the present invention to provide highly reliable data indicating a bone condition.

It is another object of the present invention to provide an apparatus and method for assessing a bone by obtaining a reference frequency for each patient, at which the attenuation factor of the transmitted ultrasonic wave is minimum, based on his personal attenuation spectrum.

It is a further object of the present invention to provide a gradient of the attenuation spectrum of an ultrasonic wave having passed through the bone and a density index value (that is, a gradient of the attenuation spectrum per unit thickness of the bone), on the basis of the reference frequency which is different among individuals.

In order to achieve the aforesaid objectives, a bone assessment apparatus of the present invention comprises (a) a means for transmitting an ultrasonic wave to the bone to be assessed, (b) a means for receiving the ultrasonic wave which has passed through and been attenuated by the bone, (c) a means for providing an attenuation spectrum of the ultrasonic wave based on a spectrum of the transmitted ultrasonic wave and a spectrum of the received ultrasonic wave, (d) a means for determining a reference frequency peculiar to the patient, based on the attenuation spectrum, at which the attenuation factor of the ultrasonic wave having passed through the bone is minimum, and (e) a calculation means for calculating a gradient of the attenuation spectrum at a predetermined frequency band between the reference frequency and a predetermined frequency which is higher than the reference frequency.

Under this structure, an ultrasonic wave having a broad frequency band is transmitted to the bone to be assessed by the transmitting means, and received at the receiving means after passing through the bone. The attenuation spectrum providing means provides an attenuation spectrum by subtracting the spectrum of the received wave from that of the transmitted wave. The reference frequency determining section determines a reference frequency at which the attenuation factor is minimum, and the gradient calculating section computes a gradient of the attenuation spectrum on the basis of the reference frequency.

Thus, the most appropriate part for a bone assessment is extracted from the attenuation spectrum for each patient on the basis of the reference frequency peculiar to the patient to compute a gradient of the attenuation spectrum and identify a person suffering from a bone disorder. In this way, the bone assessment apparatus of the present invention can provide an accurate diagnosis of the bone.

The gradient of the attenuation spectrum can be obtained by calculating a difference between two attenuation factors, one being at the reference frequency and the other being at a different frequency which is spaced apart from the reference frequency by a predetermined value, and dividing the above difference by the predetermined value.

In another aspect of the present invention, the bone assessment apparatus further comprises a means for calculating a thickness of the bone to be assessed in the direction of the ultrasonic wave transmission and a density index computing means for providing a gradient per unit thickness by dividing the gradient of the attenuation spectrum by the thickness of the bone to be assessed.

The gradient of the attenuation spectrum indicates a volume of the bone which then supplies information about the density of the bone. When the trabecula become coarse, the attenuation factor at higher frequencies decreases in comparison with that of a healthy trabecula, and therefore the gradient of the attenuation spectrum becomes gentle. Since, in the embodiment of the present invention, the frequency band for calculating a gradient of the attenuation spectrum is set on the basis of the reference frequency peculiar to each patient, the precise gradient of the attenuation spectrum and a value in connection with the bone density can be substantially obtained.

BRIEF DESCRIPTION OF THE DRAWINGS

The above and other objects, advantages and features of this invention will be more fully understood from the following detailed description, taken in conjunction with the drawings, of which.

DESCRIPTION OF THE PREFERRED EMBODIMENTS

The preferred embodiments of the present invention will now be described with reference to the drawings.

First of all, the principle of calculation of a gradient of the attenuation spectrum will be explained.

Figure 2A:
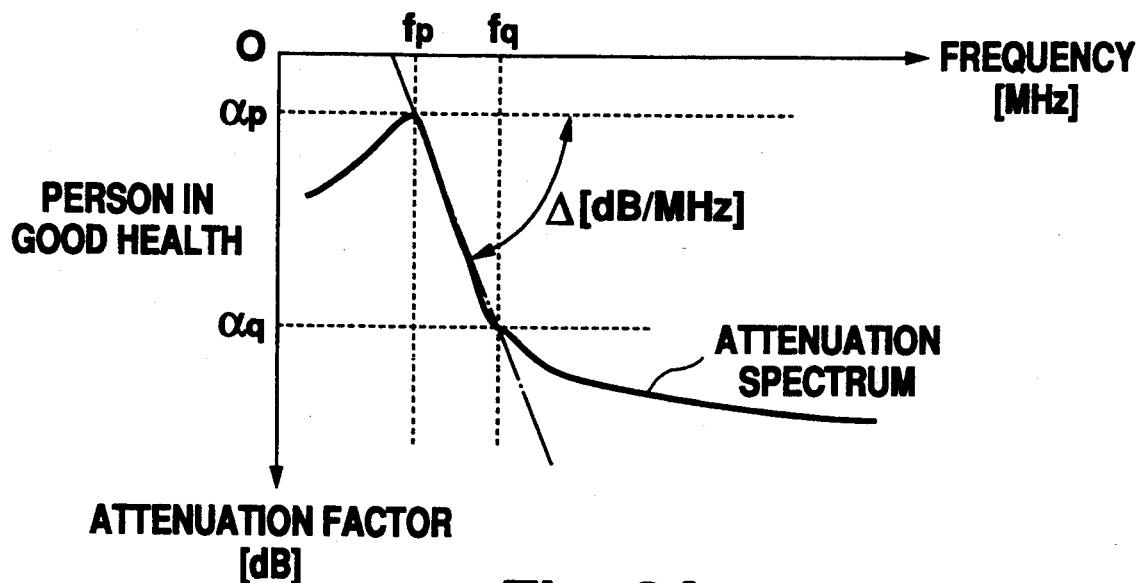
FIG. 2A shows an attenuation spectrum of an ultrasonic wave which has passed through a healthy bone.
Figure 2B:
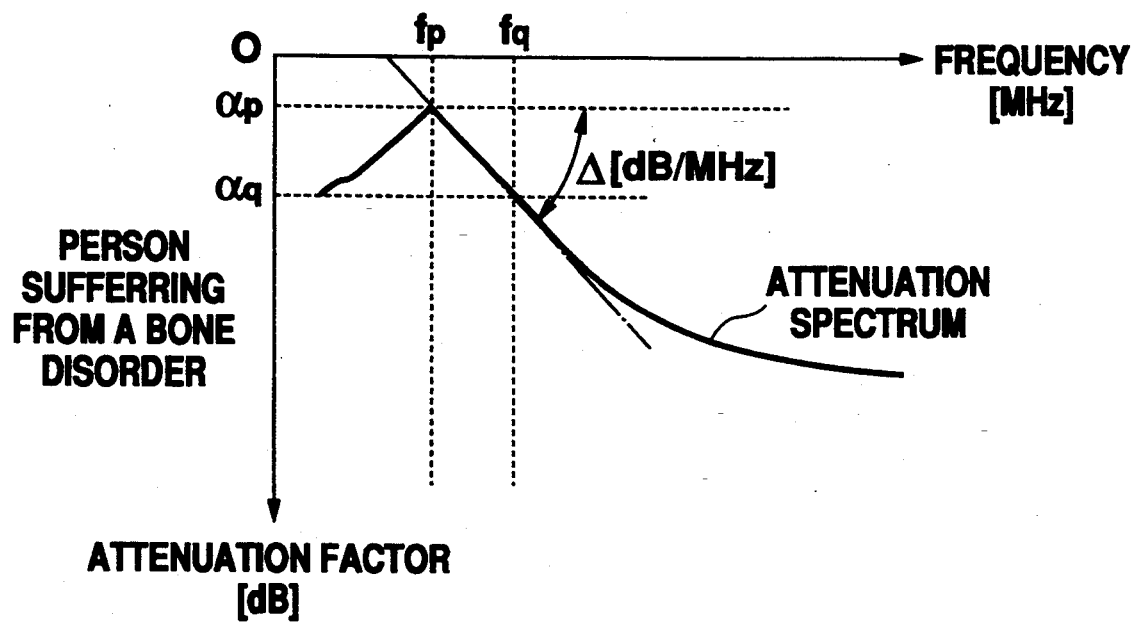
FIG. 2B shows an attenuation spectrum of an ultrasonic wave which has passed through a non-healthy bone.

In FIGS. 2A and 2B, the attenuation spectrums of ultrasonic waves which have passed through a bone is shown with frequency vs. attenuation factor. The attenuation spectrum is obtained by subtracting a spectrum of a received wave from that of a transmitted wave. In each chart, the lower portion of the Y axis indicates a greater attenuation factor.

FIG. 2A shows a typical attenuation spectrum of a person in good health, while FIG. 2B shows a typical attenuation spectrum of a person suffering from a bone disease. A reference frequency $f_p$ at which the attenuation factor is minimum (i.e. at the peak of the spectrum) is different among individuals.

A gradient $\Delta$ of the attenuation spectrum is calculated from an attenuation factor $\alpha_p$ at the reference frequency $f_p$ and an attenuation factor $\alpha_q$ at a different frequency $f_q$ which is spaced apart from the reference frequency $f_p$ by a predetermined value. Namely, the gradient $\Delta$ of the attenuation spectrum is obtained on the basis of the reference frequency.

As is shown in FIG. 2A, in the case of a person in good health, the gradient $\Delta$ of the attenuation spectrum is relatively sharp between the reference frequency $f_p$ and a higher frequency $f_q$ because the density of trabecula of the person in good health is relatively high and the volume of bone is large. In other words, the attenuation factor becomes abruptly greater at the higher frequency. On the other hand, in the case of a person suffering from a bone disorder such as osteoporosis, the gradient $\Delta$ of the attenuation spectrum is gentle at the same frequency band, i.e. between the reference frequency $f_p$ and a higher frequency $f_q$, as shown in FIG. 2B, because the density of trabecula is relatively low and the volume of bone is decreased. This means that the attenuation factor at the higher frequency is smaller than that of those in good health.

According to this principle, it become possible to estimate the density of a bone by calculating the gradient $\Delta$ of the attenuation spectrum of the ultrasonic wave which has passed through the bone.

The gradient $\Delta$ of the attenuation spectrum is calculated by using the following equation (1):

$$\Delta = (\alpha_p - \alpha_q)/(f_p - f_q) \tag{1}$$

where, the attenuation factor $\alpha$ is represented as a negative value.

In the above equation (1), the difference between the attenuation factor $\alpha_p$ at a reference frequency $f_p$ and the attenuation factor $\alpha_q$ at a frequency $f_q$, which is spaced apart by a predetermined value from the reference frequency, is divided by the difference between the reference frequency $f_p$ and the predetermined frequency $f_q$, thereby providing a gradient $\Delta$ of the attenuation spectrum.

Further, a density index $\rho_I$ relating to a bone density (i.e. a degree of density per unit thickness of the bone) is calculated by using the following equation (2):

$$\rho_I = \Delta / d \tag{2}$$

Thus, the density index $\rho_I$ is obtained by dividing the gradient $\Delta$ of the attenuation spectrum by the thickness d of the bone.

Figure 1:
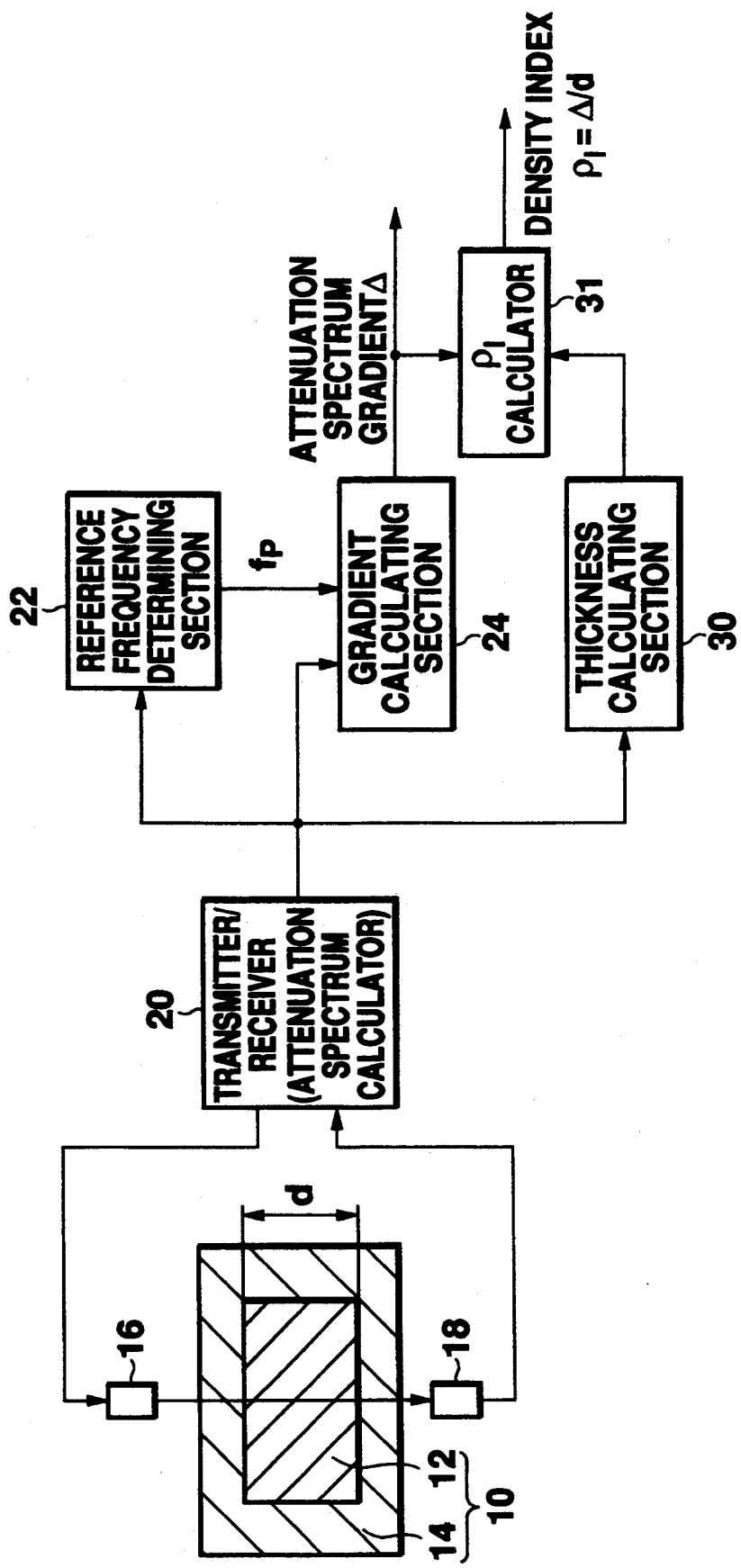
FIG. 1 is a block diagram showing an entire structure of the bone assessment apparatus of the present invention.

Hereinbelow, a bone assessment apparatus of the present invention will be described with reference to FIG. 1.

A subject 10 to be measured consists of a bone 12 and soft tissue 14. The bone 12 consists of an outer cortex and an inner spongiosa. Since a calcaneus contains a lot of spongiosa, it is likely to be affected by bone disorders. Therefore, this bone assessment apparatus is directed to the measurement and analysis of calcaneus.

A transmitting transducer 16 and a receiving transducer 18 are positioned at either side of the subject 10 to be measured, respectively. These transducers 16, 18 are connected to a transmitter/receiver 20 so that a transmission signal is supplied to the transmitting transducer 16 and a received signal is output from the receiving transducer 18 to the transmitter/receiver 20. In order to obtain an attenuation spectrum, it is preferable to transmit a broad band ultrasonic wave having a central frequency of, for example, around 500 kHz.

The transmitter/receiver 20 functions as an attenuation spectrum calculator for providing an attenuation spectrum as shown in FIGS. 2A and 2B based on the difference between the spectrum of the transmitted wave and the spectrum of the received wave. The calculated data is output to a reference frequency determining section 22, a gradient calculating section 24 and a thickness calculating section 30. The reference frequency determining section 22 determines a reference frequency $f_p$ at which the attenuation factor is minimum in the attenuation spectrum of FIGS. 2A and 2B, the data of which is then fed to the gradient calculating section 24.

The gradient calculating section 24 further receives the data corresponding to $f_q$, $\alpha_p$, and $\alpha_q$ which are shown in FIGS. 2A and 2B, and executes the equation (1) to output the gradient $\Delta$ of the attenuation spectrum.

The thus obtained gradient $\Delta$ of the attenuation spectrum indicates a degree of density of the bone, as has already been mentioned, and is an index value reflecting the bone structure.

The thickness calculating section 30 carries out the same calculation as is performed by the bone assessment apparatus disclosed in commonly assigned U.S. Ser. No. 063,779. Namely, the thickness calculating section 30 detects a position of the bone surface based on the wave form of a received signal, which represents an ultrasonic wave having passed through or been reflected at the bone, and calculates a thickness of the bone.

The $\rho_I$ calculator 31 provides a density index value which is a gradient of the attenuation spectrum per unit thickness, by calculating the equation (2), i.e. dividing the gradient $\Delta$ of the attenuation spectrum by the bone thickness d.

In this embodiment, the gradient $\Delta$ of the attenuation spectrum and the density index $\rho_I$ are displayed on a display (not shown).

As is shown in FIG. 2B, the gradient $\Delta$ of the attenuation spectrum of a person suffering from a bone disorder is gentle in comparison with that of a person in good health. For this reason, setting a predetermined threshold value K in the gradient $\Delta$ of the attenuation spectrum and determining if the measured value is above (meaning the bone is in good condition) or below (meaning the bone is suffering from a disorder) the threshold K allows easy diagnosis of a bone disorder.

The value of $(f_p - f_q)$ is preferably set between 1 MHz and 2 MHz considering the characteristics of the attenuation spectrum. In this embodiment, $(f_p - f_q)$ is set at 1.6 MHz.

As has been described, according to the present invention, a gradient $\Delta$ of the attenuation spectrum of a transmitted ultrasonic wave and a density index $\rho_I$ as a gradient of the attenuation spectrum per unit thickness can be calculated based on the appropriate reference frequency which is different among patients, which allows a more precise diagnosis of the bone.

Although the invention has been described by exemplifying a preferred embodiment, it is not limited to the embodiment, and various changes and modifications within the principle and the scope of the invention will be apparent for those skilled in the art.

What is claimed is:

1. A bone assessment apparatus for transmitting an ultrasonic wave through a bone to be assessed to diagnose the bone of a patient, comprising:
   (a) means for transmitting an ultrasonic wave to the bone to be assessed;
   (b) means for receiving the ultrasonic wave which has passed through and been attenuated by the bone;
   (c) means for providing an attenuation spectrum of the ultrasonic wave based on a spectrum of the transmitted ultrasonic wave and a spectrum of the received ultrasonic wave;
   (d) means for determining a reference frequency peculiar to the patient, based on the attenuation spectrum, at which the attenuation factor of the ultrasonic wave having passed through the bone is minimum; and
   (e) calculation means for carrying out the bone assessment, based on the attenuation factor at the reference frequency and the attenuation factor at a different frequency which is spaced apart by a predetermined value from the reference frequency.

2. A bone assessment apparatus of claim 1, wherein said calculation means carries out the bone assessment based on the attenuation factor at the reference frequency and the attenuation factor at a different frequency which is higher by a predetermined value than the reference frequency.

3. A bone assessment apparatus of claim. 2, wherein said calculation means carries out the bone assessment on the basis of a gradient of the attenuation spectrum at the frequency band between the reference frequency and said higher frequency, the gradient of the attenuation spectrum being calculated from the attenuation factor at the reference frequency and the attenuation factor at said higher frequency.

4. A bone assessment apparatus of claim 3, wherein said calculation means calculates the gradient of the attenuation spectrum by dividing the difference between the attenuation factor at the reference frequency and the attenuation factor at said higher frequency, by said predetermined value.

5. A bone assessment apparatus of claim 4, wherein said predetermined value is set between 1 MHz and 2 MHz.

6. A bone assessment apparatus of claim 3, wherein said calculation means comprises a thickness calculator for calculating a thickness of the bone to be assessed in the direction of the ultrasonic wave transmission and a density index calculator for calculating, based on said gradient of the attenuation spectrum and said thickness of the bone, a gradient spectrum per unit thickness of the bone in the direction of the ultrasonic wave transmission.

7. A bone assessment apparatus of claim 6, wherein said density index calculator obtains the gradient of the attenuation spectrum per unit thickness of the bone by dividing the gradient of the attenuation spectrum by said thickness of the bone.

8. A method for assessing a bone of a patient by transmitting an ultrasonic wave through a bone to be assessed, comprising the steps of:
   (a) transmitting an ultrasonic wave to the bone to be assessed;
   (b) receiving the ultrasonic wave which has passed through and been attenuated by the bone;
   (c) providing an attenuation spectrum of the ultrasonic wave based on a spectrum of the transmitted ultrasonic wave and a spectrum of the received ultrasonic wave;
   (d) determining a reference frequency peculiar to the patient, based on the attenuation spectrum, at which the attenuation factor of the ultrasonic wave having passed through the bone is minimum; and
   (e) calculating a gradient of the attenuation spectrum at a frequency band between the reference frequency and a different frequency which is higher by a predetermined value than the reference frequency, based on the attenuation factor at the reference frequency and the attenuation factor at said higher frequency.

9. A bone assessing method of claim 8, wherein said calculating step (e) includes a calculation of said gradient of the attenuation spectrum by dividing the difference between the attenuation factor at the reference frequency and the attenuation factor at said higher frequency by said predetermined value.

10. A bone assessment method of claim 9, further comprising a step of calculating a thickness of the bone to be assessed in the direction of the ultrasonic wave transmission, and a step of providing a density index value of the bone by calculating a gradient of the attenuation spectrum per unit thickness of the bone based on the gradient of the attenuation spectrum and the thickness of the bone.

11. A bone assessment apparatus for transmitting an ultrasonic wave through the bone of a patient to be assessed to provide a bone assessment, comprising:

(a) means for transmitting an ultrasonic wave to the bone to be assessed;
(b) means for receiving the ultrasonic wave which has passed through and been attenuated by the bone;
(c) means for providing an attenuation spectrum of the transmitted ultrasonic wave;
(d) means for determining a reference frequency peculiar to the patient at which the attenuation factor is minimum in the attenuation spectrum; and
(e) means for calculating a gradient of the attenuation spectrum at a frequency band which is higher than the reference frequency based on said reference frequency.

* * * * *